United States Patent
Beckmann

(10) Patent No.: US 7,146,858 B2
(45) Date of Patent: Dec. 12, 2006

(54) VIBRATION SENSING DEVICE

(75) Inventor: Uwe L. Beckmann, Chapel Hill, NC (US)

(73) Assignee: Search Systems, Incorporated, Bakersfield, CA (US)

(*) Notice: Subject to any disclaimer, the term of this patent is extended or adjusted under 35 U.S.C. 154(b) by 94 days.

(21) Appl. No.: 10/888,107

(22) Filed: Jul. 9, 2004

(65) Prior Publication Data

US 2005/0011268 A1   Jan. 20, 2005

Related U.S. Application Data

(60) Provisional application No. 60/487,153, filed on Jul. 14, 2003.

(51) Int. Cl.
*G01N 29/00* (2006.01)
(52) U.S. Cl. .................................. 73/649; 73/591
(58) Field of Classification Search .................. 73/649, 73/587, 661, 584, 591, 632, 652, 1.82
See application file for complete search history.

(56) References Cited

U.S. PATENT DOCUMENTS

| | | | | |
|---|---|---|---|---|
| 4,458,536 A | * | 7/1984 | Ahn et al. ..................... 73/652 |
| 4,891,611 A | * | 1/1990 | Frerking ..................... 331/158 |
| 4,991,439 A | * | 2/1991 | Betts ........................... 73/587 |
| 5,224,380 A | * | 7/1993 | Paik ............................ 73/510 |
| 6,634,472 B1 | * | 10/2003 | Davis et al. ................. 188/378 |
| 6,661,346 B1 | * | 12/2003 | Wood et al. ................. 340/601 |

* cited by examiner

*Primary Examiner*—Hezron Williams
*Assistant Examiner*—Jacques M Saint-Surin

(57) ABSTRACT

This invention relates to the design of sensors for detecting vibrations in collapsed structures. The sensor comprises a cube-shaped housing and a transducer attached internally between two opposite corners of the housing. The response of the sensor is fairly independent of which side of the housing is coupled to the collapsed structure and the sensor can also detect vibrations which occur in any signal axis of the structure.

5 Claims, 1 Drawing Sheet

VIBRATION SENSING DEVICE

This is a Non-Provisional Application claiming the benefit of co-pending Provisional Application No. 60/487,153 filed Jul. 14, 2003.

BACKGROUND OF THE INVENTION

1. Field of the Invention

This invention relates generally to the design of sensors for detecting structure borne sound, and more particularly, to sensing devices for detecting sound generated by persons trapped in collapsed structures.

2. Discussion of the Prior Art

Thousands of people are killed or injured every year in building collapses caused by earthquakes, explosions, or other disasters. Immediately after a disaster, it is important to search the collapsed structures for live victims. A common method of locating live victims is to listen for movement or tapping sounds. This invention relates to the design of electrically amplified listening devices for detecting structure borne vibrations.

In an electrically amplified listening device, an acoustic/seismic sensor is attached to the rubble pile. The sensor consists of a housing that protects the speakers or headphones or displayed on a meter, barograph or chart recorder. A search specialist listens to the generated sounds and reviews the display and determines if a victim is present.

The usefulness and accuracy of the listening device is determined to a large extent by the design of the sensor and the transducer used. Transducers can measure position, velocity or acceleration of the structure and these transducers are sensitive only along a single axis. When the direction of the vibration is not in line with the axis of the transducer, the signal is attenuated. If the direction of the vibration is orthogonal to the transducer axis, the vibration will not be picked up at all. Therefore, it would be desirable to have a transducer which is a sensitive long multiple axis.

One solution to this problem is to have multiple transducers each aligned along a different axis in the sensor. Although this is possible, multiple transducers increase the size and expense of the sensor. A better solution is to have a single axis transducer that can pick up vibrations along multiple axes, and this is the object of this invention.

Another difficulty in locating trapped victims is the uneven nature of the rubble pile. The rubble can be oriented at random angles and the searcher should be free to attach to the sensor the rubble in the most convenient fashion. This requires that the sensor be able to function at a variety of angles and orientations and have multiple surfaces that can couple to the rubble. Furthermore, the amplitude of the detected signal should be independent of the specific orientation of the sensor relative to the rubble pile.

This invention relies upon the fact that rectangular plates and beams are the most common building materials used. Vibrations in these plates or beams are usually aligned along one axis, sometimes aligned along two axes, but very rarely aligned along all three axes. This invention uses a cube-shaped housing with the transducer placed diagonally between two opposite corners. This ensures that the transducer is at an angle of approximately 45 degrees relative to the surface of the plate or beam and the detected signal will be invariant to which side of the housing is placed on the surface. Such a sensor is guaranteed to pick up all vibrations that are aligned along a single axis of the plate or beam.

SUMMARY OF THE INVENTION

It is an object of the invention is to provide a listening device comprising a housing and a transducer disposed within the housing for sensing vibrations caused by victims trapped within a collapsed structure.

Another object of the invention is to provide a device of the aforementioned character that further includes means for amplifying the vibrations sensed by the transducer and then for reproducing the amplified vibrations via speakers, headphones or the like, or alternatively for displaying the amplified vibrations on a meter, a barograph, a chart recorder or the like.

Another object of the invention is to provide a listening device of the type described in the preceding paragraphs in which the housing is generally cube-shaped and in which the sensor is uniquely mounted diagonally within the cube-shaped structure at an angle of approximately 45 degrees relative to the surface to which the device is engaged.

DESCRIPTION OF THE INVENTION

Figure 1:
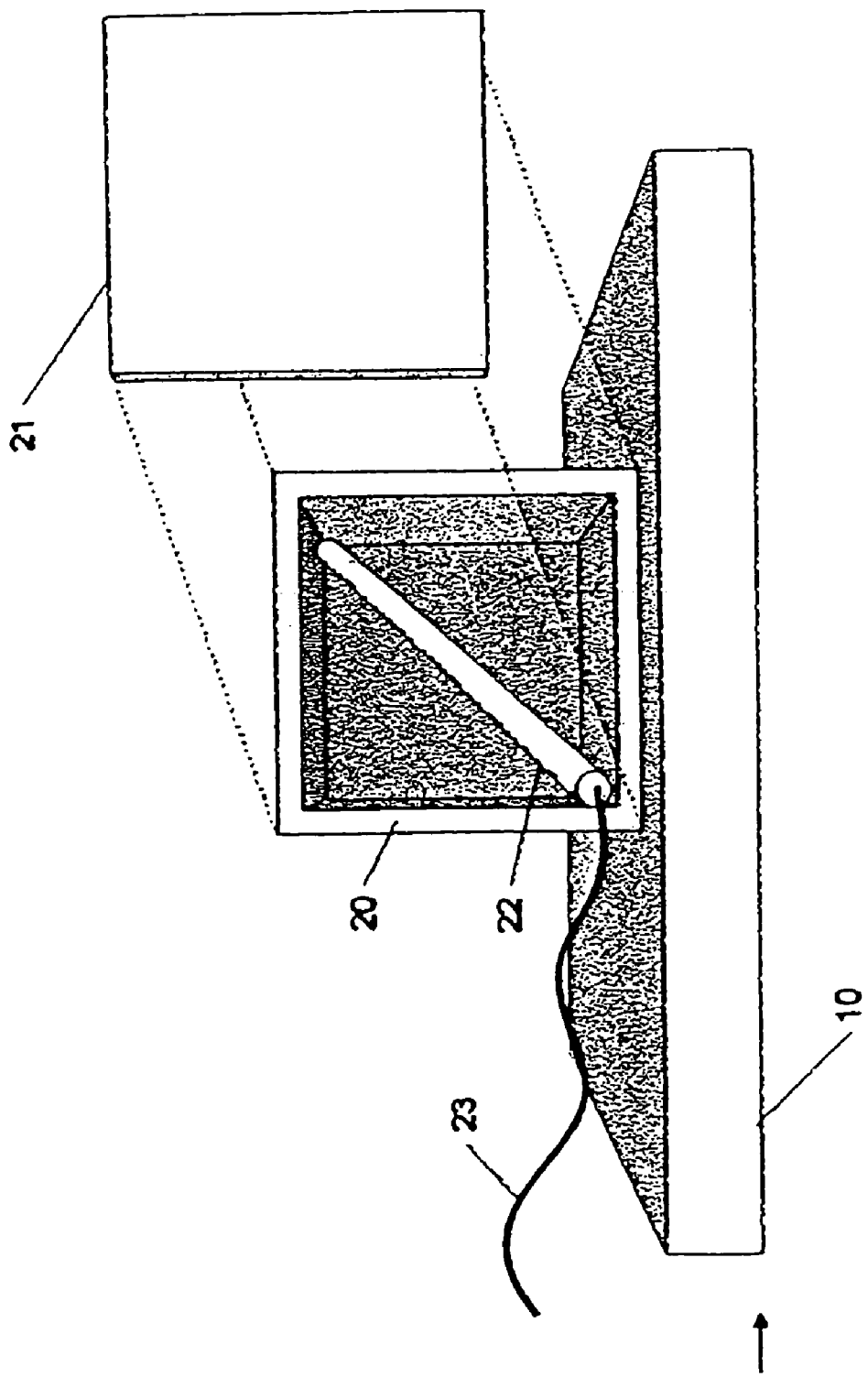
FIG. 1 is an exploded view of the cube-shaped sensor housing with internal transducer of the present invention.

Referring now to the drawings, and more particularly FIG. 1, a vibrating beam 10 with a sensor attached to it. The sensor consists of a cube-shaped housing 20 and 21, a transducer 22 that is located internally to the housing and rigidly attached to it and a cable 23 for carrying the sensor signal to the searcher.

The X, Y and Z axes shown in FIG. 1 are consistent with the orientation of the beam. If the transducer 22 is aligned along the X-axis, then it will not pick up any vibrations along the Y and Z axes. If the transducer 22 is aligned along the Y-axis, then it will not pick up any vibrations in the X and Z axes. Similarly, if the transducer 22 is aligned along the Z-axis, it will not pick up any vibrations in the X and Y axes.

In accordance with the principles of the present invention, the transducer 22 is aligned internally in the housing at an angle of 45 degrees relative to the X, Y and Z axes. When mounted in this diagonal fashion, the sensor will always respond to vibration in any single axis. Although the response will be attenuated by roughly three dB relative to a transducer perfectly aligned with the axis of vibration, it is better to have a slightly attenuated signal rather than to miss it completely.

The cube-shaped housing 20 also has 6 sides as shown in FIG. 1 and any one of these sides may be used to couple with the rubble pile. Given the symmetrical manner in which the transducer is oriented in the housing, the transducer will always be at a 45 degree angle to the X, Y and Z axes of the housing irrespective of which of the 6 sides is used for coupling the device to the selected structure of the rubble pile. Therefore, the response of the sensor will be insensitive to its specific orientation in the rubble pile.

I claim:

1. A device for sensing vibration in a structure made up of structural members, said device comprising:
   (a) a generally cube-shaped housing having a plurality of the exterior walls defining an interior space, one of said walls being disposable in engagement with a structural member of the structure, said interior space having X, Y and Z axes; and
   (b) sensor means disposed with said interior space and an angle of approximately 45 degrees with respect to said X, Y and Z axes for generating a signal in response to a vibration in the structure;
   (c) signal receiving means disposed externally of said interior space; and (d) signal transmission means for receiving signals from said sensor means and for transmitting said signals to said signal receiving means.

2. The device as defined in claim 1 in which said sensor means comprises a single axis transducer.

3. The device as defined in claim 1 in which said device further includes an amplifier cooperatively associated with said signal receiving means.

4. The device as defined in claim 3 in which said signal receiving means comprises a speaker.

5. The device as defined in claim 3 in which said signal receiving means comprises headphones.

\* \* \* \* \*